US011948311B2

(12) United States Patent
Cauley et al.

(10) Patent No.: US 11,948,311 B2
(45) Date of Patent: Apr. 2, 2024

(54) RETROSPECTIVE MOTION CORRECTION USING A COMBINED NEURAL NETWORK AND MODEL-BASED IMAGE RECONSTRUCTION OF MAGNETIC RESONANCE DATA

(71) Applicant: THE GENERAL HOSPITAL CORPORATION, Boston, MA (US)

(72) Inventors: Stephen Cauley, Somerville, MA (US); Melissa Haskell, Cambridge, MA (US); Lawrence Wald, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 379 days.

(21) Appl. No.: 17/442,962

(22) PCT Filed: Mar. 26, 2020

(86) PCT No.: PCT/US2020/024930
§ 371 (c)(1),
(2) Date: Sep. 24, 2021

(87) PCT Pub. No.: WO2020/198456
PCT Pub. Date: Oct. 1, 2020

(65) Prior Publication Data
US 2022/0189041 A1    Jun. 16, 2022

Related U.S. Application Data

(60) Provisional application No. 62/824,576, filed on Mar. 27, 2019.

(51) Int. Cl.
G06T 7/246    (2017.01)
G06T 3/4046    (2024.01)

(52) U.S. Cl.
CPC .............. G06T 7/251 (2017.01); G06T 3/4046 (2013.01); *G06T 2207/10088* (2013.01)

(58) Field of Classification Search
CPC ................... G06T 7/251; G06T 3/4046; G06T 2207/10088
See application file for complete search history.

(56) References Cited

U.S. PATENT DOCUMENTS

| 6,894,494 B2 * | 5/2005 | Stergiopoulos .... G01R 33/5673 324/309 |
| 7,348,776 B1 * | 3/2008 | Aksoy ................ G01R 33/5611 324/307 |

(Continued)

FOREIGN PATENT DOCUMENTS

WO    WO-2017132648 A1 *    8/2017    ......... G01R 33/5608

OTHER PUBLICATIONS

Cordero-Grande et al., 2018, "Three-Dimensional Motion Corrected Sensitivity Encoding Reconstruction for Multi-Shot Multi-Slice MRI: Application to Neonatal Brain Imaging" (pp. 1365-1376) (Year: 2018).*

(Continued)

*Primary Examiner* — Manav Seth
(74) *Attorney, Agent, or Firm* — Quarles & Brady LLP

(57) ABSTRACT

A combined physics-based and machine learning framework is used for reconstructing images from k-space data, in which motion artifacts are significantly reduced in the reconstructed images. In general, model-based retrospective motion correction techniques are accelerated using fast machine learning ("ML") steps, which may be implemented using a trained neural network such as a convolutional neural network. In this way, the confidence of a classical physics-based reconstruction is obtained with the computational benefits of an ML-based network.

17 Claims, 6 Drawing Sheets

(56) References Cited

U.S. PATENT DOCUMENTS

| | | | | |
|---|---|---|---|---|
| 7,902,825 | B2* | 3/2011 | Bammer | G01R 33/56341 |
| | | | | 324/309 |
| 8,306,299 | B2* | 11/2012 | Samsonov | G01R 33/56509 |
| | | | | 382/128 |
| 8,427,153 | B2* | 4/2013 | Hu | G01R 33/56509 |
| | | | | 324/309 |
| 9,202,272 | B2* | 12/2015 | Akcakaya | G01R 33/56509 |
| 9,788,761 | B2* | 10/2017 | Lu | A61B 5/0042 |
| 9,933,505 | B2* | 4/2018 | Pipe | G06T 11/006 |
| 10,295,640 | B2* | 5/2019 | Beck | G01R 33/4835 |
| 10,713,785 | B2* | 7/2020 | Braun | G06T 7/20 |
| 10,806,370 | B1* | 10/2020 | Brada | A61B 5/7257 |
| 10,830,855 | B2* | 11/2020 | Cai | G06T 7/20 |
| 10,996,306 | B2* | 5/2021 | Heukensfeldt Jansen | |
| | | | | G06V 10/993 |
| 11,185,249 | B2* | 11/2021 | Schlemper | G01R 33/4835 |
| 2005/0197586 | A1 | 9/2005 | Pearlman | |
| 2012/0082355 | A1* | 4/2012 | Mendes | G01R 33/56509 |
| | | | | 382/131 |
| 2014/0079305 | A1* | 3/2014 | Akcakaya | G01R 33/56509 |
| | | | | 382/131 |
| 2017/0337682 | A1 | 11/2017 | Liao et al. | |
| 2017/0372193 | A1 | 12/2017 | Mailhe et al. | |
| 2018/0210058 | A1 | 7/2018 | De Weerdt | |
| 2018/0232878 | A1 | 8/2018 | Braun et al. | |
| 2018/0260981 | A1* | 9/2018 | Gholipour-Baboli | |
| | | | | G01R 33/56341 |
| 2019/0035119 | A1* | 1/2019 | Cauley | G01R 33/5611 |
| 2021/0123999 | A1* | 4/2021 | An | G01R 33/567 |
| 2021/0225047 | A1* | 7/2021 | Pawar | G06N 3/045 |

OTHER PUBLICATIONS

Johnson et al., 2019, "Conditional generative adversarial network for 3D rigid-body motion correction in MRI", (pp. 901-910) (Year: 2019).*

International Search Report and Written Opinion for PCT/US2020/024930—dated Jun. 19, 2020.

* cited by examiner

RETROSPECTIVE MOTION CORRECTION USING A COMBINED NEURAL NETWORK AND MODEL-BASED IMAGE RECONSTRUCTION OF MAGNETIC RESONANCE DATA

CROSS-REFERENCE TO RELATED APPLICATIONS

This application is a U.S. National Stage of International Application No. PCT/US2020/024930 filed Mar. 26, 2020 which claims the benefit of U.S. Provisional Patent Application Ser. No. 62/824,576, filed on Mar. 27, 2019, and entitled "ACCELERATED RETROSPECTIVE MOTION CORRECTION USING A NEURAL NETWORK," which is herein incorporated by reference in its entirety.

STATEMENT REGARDING FEDERALLY SPONSORED RESEARCH

This invention was made with government support under MH093765, EB017337, EB015896, DA022759, and DA023427 awarded by the National Institutes of Health, and under DGE 1144152 awarded by the National Science Foundation. The government has certain rights in the invention.

BACKGROUND

Since its inception, MRI has been hindered by artifacts due to patient motion, which are both common and costly. Many techniques attempt to track or otherwise account and correct for motion during MRI data acquisition, yet few are currently used clinically due to workflow challenges or sequence disturbances. While prospective motion correction methods measure patient motion and update the acquisition coordinates on the fly, they often require sequence modifications (e.g., insertion of navigators) or external hardware tracking systems. On the other hand, retrospective methods correct the data after the acquisition, possibly incorporating information from navigators or trackers.

Data-driven retrospective approaches operating without tracker or navigator input are attractive because they minimally impact the clinical workflow. These algorithms estimate the motion parameters providing the best parallel imaging model agreement through the addition of motion operators in the encoding. Unfortunately, this approach typically leads to a poorly conditioned, nonconvex optimization problems. In addition to potentially finding a deficient local minimum, the reconstructions often require prohibitive compute times using standard vendor hardware, limiting the widespread use of the methods.

SUMMARY OF THE DISCLOSURE

The present disclosure addresses the aforementioned drawbacks by providing a method for reconstructing an image with reduced motion artifacts from k-space data acquired with a magnetic resonance imaging (MRI) system. The method includes accessing k-space data with a computer system, where the k-space data have been acquired from a subject using an MRI system, and where the k-space data contain motion errors associated with motion of the subject. A motion-corrupted image of the subject is reconstructed from the k-space data using the computer system. The motion-corrupted image is applied as an input to a trained neural network, generating output as a motion artifact image that depicts motion artifacts associated with the motion of the subject. A difference image is generated by subtracting the motion artifact image from the motion-corrupted image. Motion parameters that define one or more motion trajectories are then computed from the difference image and the k-space data. The motion-corrected image of the subject is then reconstructed by inputting the k-space data and the motion parameters to a model-based image reconstruction algorithm, generating output as the motion-corrected image. This process can be, as an example, iteratively performed until convergence to a fully motion-mitigated image.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for a combined physics-based and machine learning framework for reconstructing images from k-space data, in which motion artifacts are significantly reduced in the reconstructed images. In general, the systems and methods described in the present disclosure accelerate model-based retrospective motion correction techniques using fast machine learning ("ML") steps. In this way, the confidence of a classical physics-based reconstruction is obtained with the computational benefits of an ML-based network.

The combined physics/machine learning framework described in the present disclosure can be used to retrospectively account for patient motion in image reconstruction processes (e.g., parallel imaging reconstructions), thereby making MRI scans robust to patient motion. As a result, the number of studies that would otherwise need to be repeated because of patient motion can be greatly reduced. Further, overall scan time can be improved by limiting the use of navigators that may otherwise be needed to retrospectively correct for motion. As another advantage, the purchase of costly and difficult to use motion tracking hardware or expensive anesthesia procedures can also be avoided when using the systems and methods described in the present disclosure.

Figure 1:
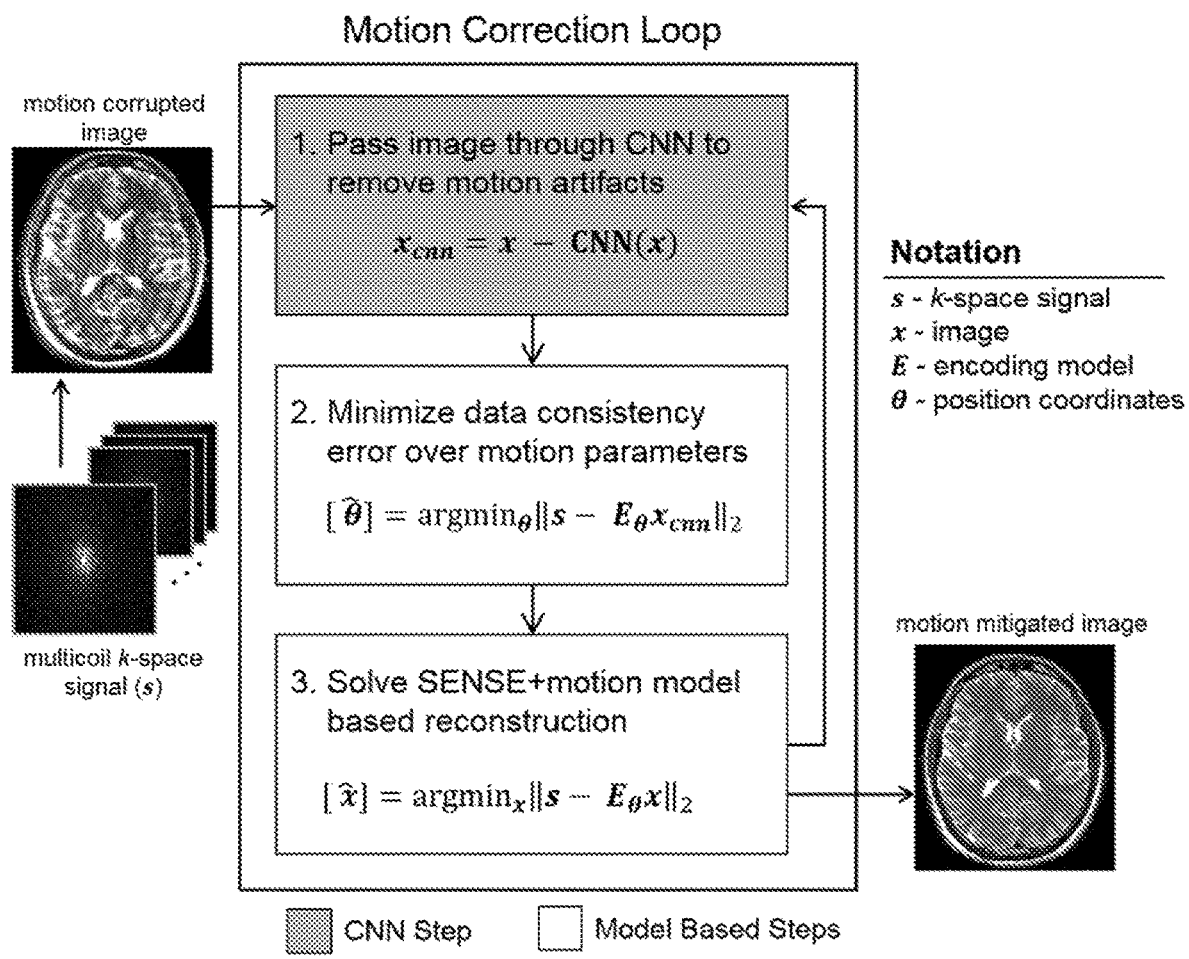
FIG. 1 shows an example workflow for a Network Accelerated Motion Estimation and Reduction ("NAMER") method for reconstructing motion-corrected images using a combined physics/machine learning framework.

An overview of an example of this Network Accelerated Motion Estimation and Reduction ("NAMER") method is shown in FIG. 1. In this example, the method is initialized with a SENSE reconstruction of the raw k-space data. The motion correction algorithm is divided into three processes that are iteratively performed: (1) an artifact detecting CNN is applied to identify motion artifacts that are subsequently removed, (2) based upon the CNN output, a non-linear optimization estimates the associated motion parameters that minimize the data-consistency error of the forward model, and (3) a model-based reconstruction is performed to generate an updated image based on the motion parameters found in step (2). As one non-limiting example, a SENSE+ motion forward model can be used for the model-based image reconstruction step. These steps are then repeated using the updated model-based reconstruction to further reduce the data consistency error and related motion artifacts.

In the artifact detecting step, motion corrupted image patches are passed into the CNN and the artifacts within the patches are detected. Two channel input data can be used to hold the real and imaginary components. The CNN can include, but is not limited to, convolutional, batch normalization, and ReLU activation layers. Training can be performed using simulated motion corrupted images based on a motion forward model using either measured or simulated motion trajectories. The artifacts detected by the CNN are then subtracted from the original input image. In this way, the CNN is used to provide an initial guess of the motion artifacts, thereby improving the conditioning of the nonconvex motion search and accelerating convergence.

Figure 2:
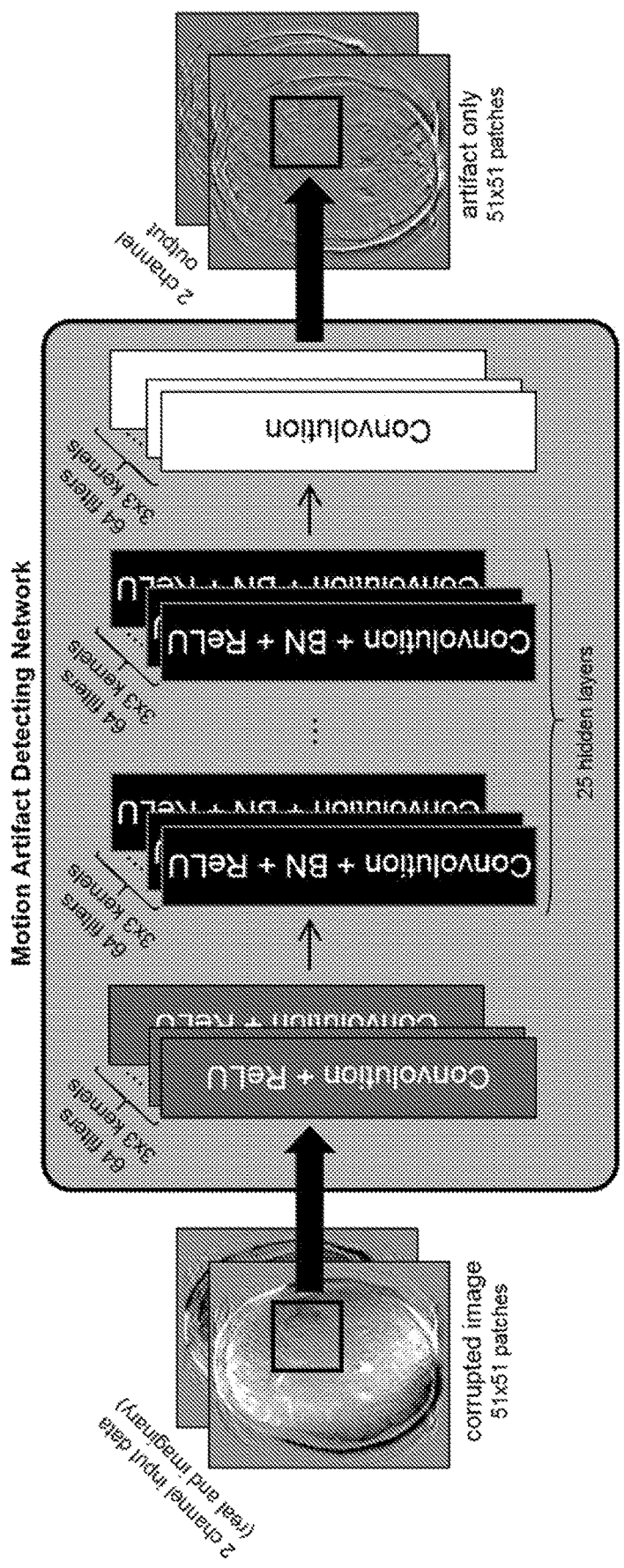
FIG. 2 shows an example convolutional neural network for motion artifact detection.

FIG. 2 shows an example CNN architecture that can be trained and implemented for detecting motion artifacts in motion-corrupted images. The network isolates the image artifacts within the two-channel (real and imaginary) motion corrupted input patch. The initial layer is a convolutional layer followed by a ReLU activation. The next 25 layers include a convolutional layer with batch normalization and ReLU activation, and the final layer is a convolution layer. Each convolutional layer uses 3×3 kernels with 64 filters. The output from the CNN, CNN(x), is a motion artifact image that contains the detected motion artifacts within the input image x. An image prior, $x_{cnn}$, can then be described mathematically as:

$$x_{cnn} = x - CNN(x)$$

This image prior is then used for the motion parameter search, as described above. The resulting motion estimate is then used to create an improved image which can be propagated as input to the CNN to initialize the next pass of the algorithm. The quality of this image estimate can significantly improve the conditioning and convergence of the nonconvex motion parameter optimization. In addition, with this high quality CNN image estimate, the motion optimization becomes separable. For instance, even though the CNN image may not represent the "ground-truth", it does contain sufficient information to guide the separable search for the motion trajectory. The separability of the motion model allows for small sub-problems to be optimized in a highly parallel fashion. This allows for a scalable extension of the model-based approach to include intra-shot (line-by-line) motion as well as the inter-shot motion. The increased computation speed also facilitates implementation on standard vendor computation hardware.

Figure 3:
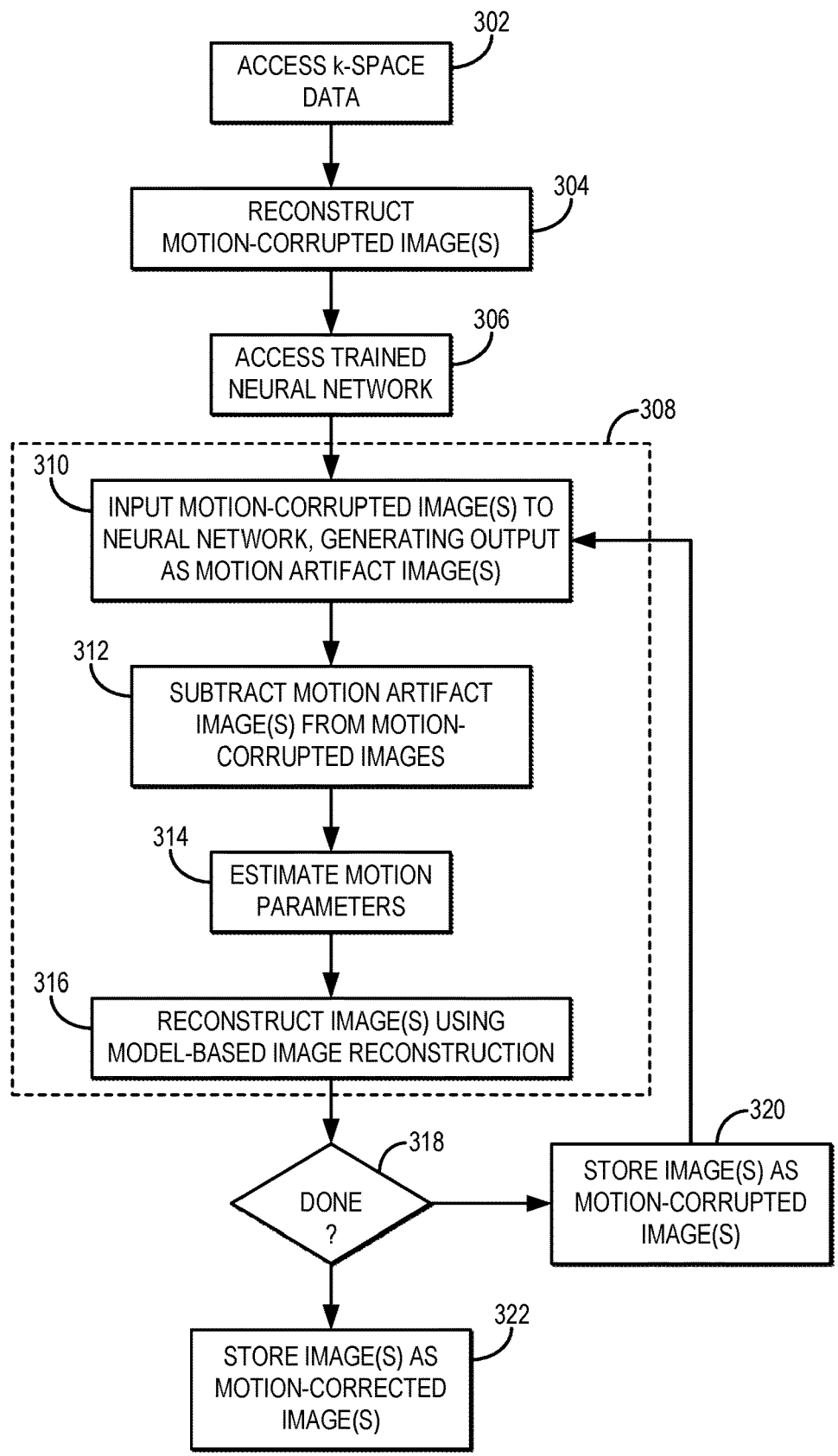
FIG. 3 is a flowchart setting forth the steps of an example method for reconstructing a motion-corrected image using the combined physics/machine learning framework described in the present disclosure.

Referring now to FIG. 3, a flowchart is illustrated as setting forth the steps of an example method for reconstructing an image of a subject in which motion artifacts are mitigated using a combined physics-based and machine learning framework.

The method includes accessing k-space data with a computer system, as indicated at step 302. Accessing the k-space may include retrieving such data from a memory or other suitable data storage device or medium. Alternatively, accessing the k-space may include acquiring such data with an MRI system and transferring or otherwise communicating the data to the computer system, which may be a part of the MRI system.

In general, the k-space data are motion-corrupted k-space data, in that the k-space data contain errors associated with motion of the subject. Images reconstructed from such motion-corrupted k-space data will include motion artifacts.

One or more motion-corrupted images are reconstructed from the k-space data, as indicated at step 304. For instance, the motion corrupted image(s) can be reconstructed using a conventional image reconstruction technique. As one example, the motion-corrupted image(s) can be reconstructed using a SENSE reconstruction.

A trained neural network (or other suitable machine learning algorithm) is then accessed with the computer system, as indicated at step 306. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, types of layers, ordering of layers, connections between layers, hyperparameters for layers) may be retrieved, selected, constructed, or otherwise accessed.

In general, the neural network is trained, or has been trained, on training data in order to detect motion artifacts in a motion-corrupted image. The neural network can be a convolutional neural network, as described above. In other instances, more sophisticated networks may be implemented. Moreover, the network parameters (e.g., patch-size, number of hidden layers, learning rate, number of filters, kernel size) can be tuned to optimize the output of the neural network.

The motion-corrupted image is then input to an iterative process for reconstructing a motion-corrected image, generally indicated as process block 308. First, the current motion-corrupted image is input to the trained neural network, generating output as a motion artifact image, as indicated at step 310. As described above, in some instances, the trained neural network can include two input channels and two output channels: one each for a real part and an imaginary part of the input and output images. In these instances, the real part and the imaginary part of the motion-corrupted image are applied to the different input channels of the trained neural network, generating output as a real part and an imaginary part of the motion artifact image on the respective output channels.

The motion artifact image is then subtracted from the current motion-corrupted image, as indicated at step 312. This difference image is used as an image prior for the motion parameter optimization. Thus, motion parameters are estimated next from the difference image, $x_{cnn}$, as indicated at step 314.

The vector containing the motion parameters, θ, can be estimated from $x_{cnn}$ through a non-linear optimization to minimize the data consistency model error between the acquired data and the forward model described by the encoding matrix. The encoding includes the effect of the motion trajectory as well as the Fourier encoding and undersampling. The encoding matrix, $E_θ$, for the motion parameters θ, can be described mathematically as:

$$E_θ = UFCT_θ R_θ \qquad (1);$$

where $R_θ$ is a rotation operator, $T_θ$ is a translation operator, C applies coil sensitivities, F is Fourier encoding, and U is a sampling operator. The motion parameters can be found by minimizing the data consistency error between the acquired k-space data, s, and the k-space data generated by applying the motion forward model $E_θ$ to the difference image:

$$[\hat{θ}] = \mathrm{argmin}_θ \|s - E_θ x_{cnn}\|_2 \qquad (2).$$

As one non-limiting example, the minimization can be performed using a quasi-Newton search.

The underlying image and motion parameters are tightly coupled, which generally prohibits the separation of the optimization variables into orthogonal subsets. This directly limits the performance of alternating methods to only 1 or 2 productive steps during each alternating pass. Advantageously, using a neural network as a precursor to optimizing the motion parameters as described in the present disclosure allows for the efficient decomposition of the optimization.

Specifically, the motion parameters, θ, which are typically optimized in a single cost function as shown in Eqn. (2), can be separated to create a set of much smaller optimization problems, where motion parameters, θ, can be independently estimated (e.g., for each shot of a pulse sequence, such as a RARE pulse sequence). In these instances, the motion parameters can then be indexed by the shot number; $θ = [θ_1, θ_2, \ldots θ_N]$ where N is the total number of shots, and each vector $θ_n$ contains the motion parameters (e.g., six rigid body motion parameters) for a given shot. The motion forward model, $E_θ$, can be reduced to only generate the subset of k-space associated with shot n, in which instances it can be denoted as $E_{θ_n}$. Similarly, the acquired data for a single shot can be denoted as $s_n$ and the cost function for a single shot is:

$$[\hat{θ}_n] = \mathrm{argmin}_{θ_n} \|s_n - E_{θ_n} x_{cnn}\|_2 \qquad (3).$$

By using Eqn. (3) instead of Eqn. (2), the number of unknowns for any optimization is decreased by a factor of N (i.e., the total number of shots). These separate minimizations can be done in parallel, which greatly improves the computational scalability of the retrospective motion correction approach.

This computational efficiency enables further refinement of the optimization variables. For instance, the cost function in Eqn. (3) can be extended to consider intra-shot motion by assigning additional motion parameters to the individual lines of k-space within a shot. Thus $θ_n$ can be expanded as $θ_n = [θ_{n,1}, θ_{n,2}, \ldots θ_{n,L}]$ for $l = 1, 2, \ldots L$ where L is the number of lines per shot (e.g., the ETL of a RARE pulse sequence). In these instances, the forward model can then be further reduced to $E_{θ_{n,l}}$ to generate the k-space data only for line l of shot n, and the signal for that line can be written as $s_{n,l}$. To find the optimal motion parameters for an individual line, the cost function becomes:

$$[\hat{θ}_{n,l}] = \mathrm{argmin}_{θ_{n,l}} \|s_{n,l} - E_{θ_{n,l}} x_{cnn}\|_2 \qquad (4).$$

The ability to selectively refine the optimization variables is advantageous because only small portions of the acquisition are likely to suffer from significant intra-shot motion. These shots show significant data consistency error and are often considered as outliers to be discarded. However, with the separable model approach described in the present disclosure, the model can be dynamically expanded. The parallel optimizations in Eqn. (3) can be performed for each shot, and then shots that have large data consistency after this first pass can then be improved upon using Eqn. (4). By using this multiscale optimization for the motion parameters, the length of θ can vary depending on how many shots require intra-shot correction. Similar to Eqn. (2), a quasi-Newton search can be implemented for the optimization in Eqns. (3) and (4).

Referring still to FIG. 3, after the motion parameters are estimated they are input with the original k-space data to a model-based image reconstruction algorithm, generating output one or more reconstructed images, as indicated at step 316. For example, using the raw k-space data, s, and the current estimate for the motion trajectory, θ, a linear least squares image reconstruction problem can be solved using a conjugate gradient method to find the image, x:

$$[\hat{x}] = \mathrm{argmin}_x \|s - E_θ x\|_2 \qquad (5).$$

The reconstructed image(s) are evaluated at decision block 318 to determine whether further motion correction should be implemented. For instance, the steps in process block 308 can be repeated until a stopping criterion is met. As one example, the stopping criterion can be a maximum number of iterations. As another non-limiting example, the stopping criterion can be when the change in x is below a given threshold. When the stopping criterion is not satisfied, then the reconstructed images are stored as the current motion-corrupted images at step 320 and used as an input to a subsequent iteration of process block 308. When the stopping criterion is satisfied, then the reconstructed images are stored as the motion-corrected images, as indicated at step 322. The reconstructed images can be displayed to a user, stored for later use or further processing, or both.

Figure 4:
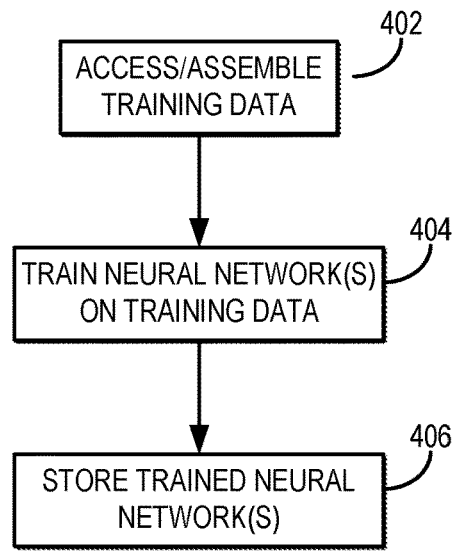
FIG. 4 is a flowchart setting forth the steps of an example method for training a machine learning algorithm, such as a neural network, to detect motion artifacts in a motion-corrupted image.

Referring now to FIG. 4, a flowchart is illustrated as setting forth the steps of an example method for training one or more neural networks (or other suitable machine learning algorithms) on training data, such that the one or more neural networks are trained to receive input as motion-corrupted images in order to generate output as motion artifact images that contain motion artifacts present in the motion-corrupted images.

In general, the neural network(s) can implement any number of different neural network architectures. For instance, the neural network(s) could implement a convolutional neural network. In some instances, the neural network(s) may implement deep learning. Alternatively, the neural network(s) could be replaced with other suitable machine learning algorithms, such as those based on supervised learning, unsupervised learning, deep learning, ensemble learning, dimensionality reduction, and so on.

The method includes accessing training data with a computer system, as indicated at step 402. Accessing the training data may include retrieving such data from a memory or other suitable data storage device or medium. Alternatively, accessing the training data may include acquiring such data with an MRI system and transferring or otherwise communicating the data to the computer system, which may be a part of the MRI system. Additionally or alternatively, the method can include assembling training data from k-space data and/or magnetic resonance images using a computer system. This step may include assembling the k-space data and/or magnetic resonance images into an appropriate data structure on which the neural network(s) can be trained.

In general, the training data can include k-space data and/or magnetic resonance images that have been manipulated to include simulated motion. For example, the training data can include k-space data that have been manipulated using a forward model to simulate the effects of realistic patient motion trajectories, thereby resulting in simulated motion-corrupted images. The motion trajectories used to simulate the patient motion can be simulated, or may be created using data augmentation (e.g., shifting and scaling) of time-series registration information from fMRI scans, or the like.

The neural network, which may be a residual learning CNN, attempts to identify the motion artifacts using a loss function (e.g., an $L_2$-norm loss function) against the motion-corrupted input image minus the ground truth image. As one non-limiting example, ten evenly spaced slices from the four healthy subjects can be used, and each slice was corrupted by ten different motion trajectories. In this example, 400 motion examples were thus generated for use as training data.

The training data can be refined through the exclusion of motion-corrupted images with root mean square error ("RMSE") compared to ground truth that is between a specified range. As one example, motion-corrupted images with an RMSE compared to ground truth greater than 0.50 or less than 0.12 can be excluded from the training data. To reduce the memory and computational footprint, a number of random cases can also be dropped to limit the training size.

Assembling the training data may also include dividing each image in the training data into patches. For instance, each motion-corrupted image in the training data can be divided into patches. As one non-limiting example, the images can be divided into patches each having a size 51×51 with an overlapping region of 10 voxels. For each image, a number of the generated patches can be randomly selected for final inclusion in the training data. In one example, the total number of motion corrupted patches in a training data set was 375,000. From this set of patches, 300,000 were used for training and 75,000 were used for validation (i.e., achieving an 80/20 training/validation split).

Referring still to FIG. 4, one or more neural networks (or other suitable machine learning algorithms) are trained on the training data, as indicated at step 404. In general, the neural network can be trained by optimizing network parameters (e.g., weights, biases, or both) based on minimizing a loss function. As one non-limiting example, the loss function may be a mean squared error loss function. The neural network can be trained using an optimizer such as the Adam optimizer. In one non-limiting example, a learning rate of $1\times10^{-4}$ and a mean squared error loss function was used.

Training a neural network may include initializing the neural network, such as by computing, estimating, or otherwise selecting initial network parameters (e.g., weights, biases, or both). Training data can then be input to the initialized neural network, generating output as motion artifact images. The quality of the output can then be evaluated, such as by passing the output to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

The one or more trained neural networks are then stored for later use, as indicated at step 406. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers) may be stored.

As described above, a scalable retrospective motion correction method that effectively integrates a motion artifact detecting neural network within a model-based motion estimation framework is provided. The image estimates generated by the neural network advantageously allow for separation of the motion parameter search into either individual shots or individual k-space lines. The small optimization problems can be efficiently computed in a parallel fashion. This results in a highly scalable algorithm that has the potential for clinical acceptance. In addition, the separability of the motion optimization facilitates efficient refinement of the model to consider motion disturbances that can occur within a shot. These specific shots can be identified due to their large data consistency error, and line-by-line motion correction can be applied. The separability afforded by the methods described in the present disclosure also allows for focusing on improving the motion correction in only the troubled regions, thereby reducing the overall computational burden.

The model-based reconstruction described in the present disclosure also allows for relaxing concerns about the accuracy, robustness, and predictability of a purely neural network-based motion correction. Although the CNN described in the present disclosure is able to reduce motion artifacts across all slices from a previously unobserved data set, it may not be able to completely remove all of the artifacts. However, the CNN output is accurate enough to both improve the convergence of the reconstruction and promote the separability of the motion parameter optimization. Through the inclusion of more diverse and larger training data sets, it is expected that these benefits will grow.

The motion model separability described in the present disclosure could also accelerate the determination of which individual lines are good candidates for removal or re-weighting. The CNN motion-mitigated image (i.e., the difference between the input motion-corrupted image and the output motion artifact image) itself can provide supplemental information used to dampen the effects of the outliers. Beyond the rigid-body motion correction described in the present disclosure, the NAMER framework can also be extended to non-rigid motion correction, such as that used for body imaging.

Figure 5:
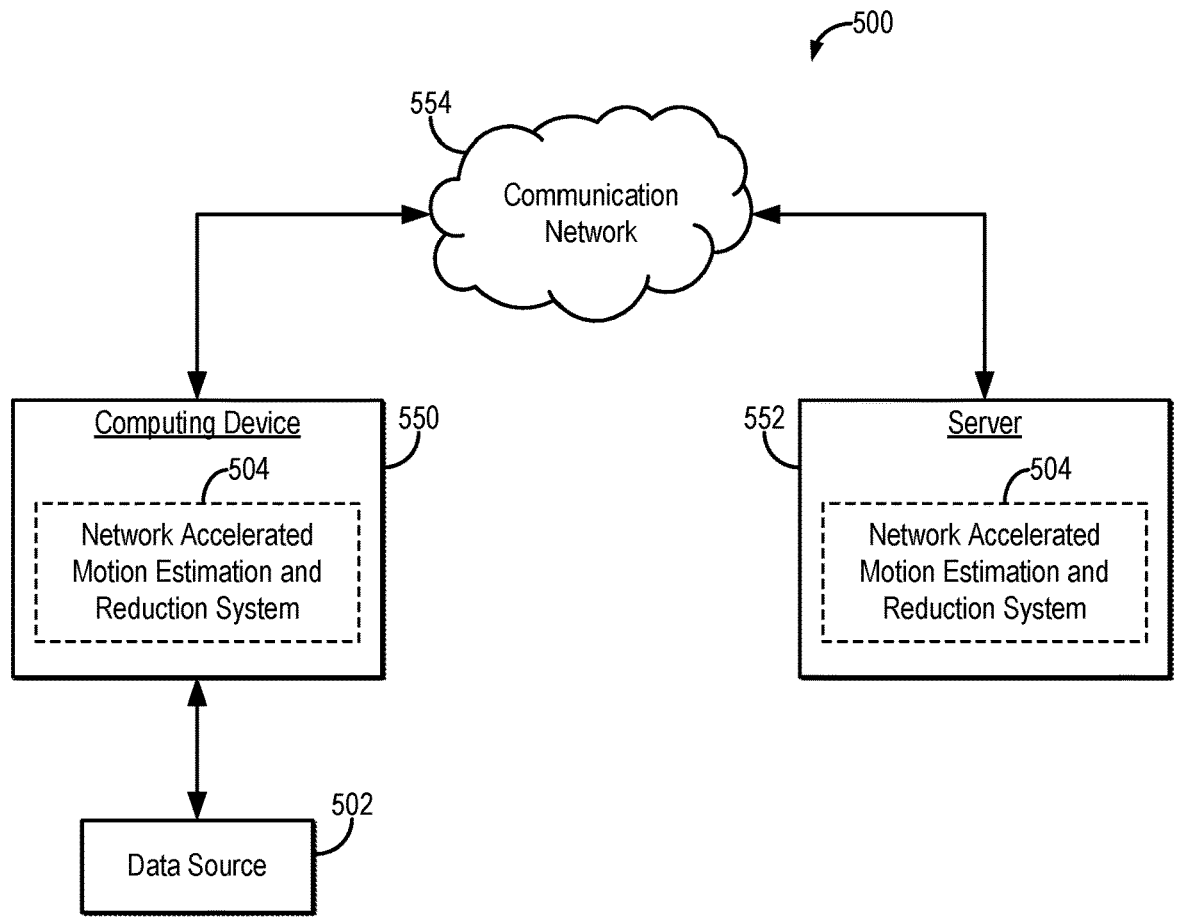
FIG. 5 is a block diagram of a system for reconstructing motion-corrected images using a combined physics/machine learning framework.

Referring now to FIG. 5, an example of a system 500 for reconstructing motion-corrected images using a combined physics/machine learning framework in accordance with some embodiments of the systems and methods described in the present disclosure is shown. As shown in FIG. 5, a computing device 550 can receive one or more types of data (e.g., k-space data, training data) from data source 502. In some embodiments, computing device 550 can execute at least a portion of a network accelerated motion estimation and reduction system 504 to reconstruct motion-corrected images from data received from the data source 502.

Additionally or alternatively, in some embodiments, the computing device 550 can communicate information about data received from the data source 502 to a server 552 over a communication network 554, which can execute at least a portion of the network accelerated motion estimation and reduction system. In such embodiments, the server 552 can return information to the computing device 550 (and/or any other suitable computing device) indicative of an output of the network accelerated motion estimation and reduction system 504.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, data source 502 can be any suitable source of image data (e.g., measurement data, images reconstructed from measurement data), such as an MRI system, another computing device (e.g., a server storing image data), and so on. In some embodiments, data source 502 can be local to computing device 550. For example, data source 502 can be incorporated with computing device 550 (e.g., computing device 550 can be configured as part of a device for capturing, scanning, and/or storing images). As another example, data source 502 can be connected to computing device 550 by a cable, a direct wireless link, and so on. Additionally or alternatively, in some embodiments, data source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 554 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
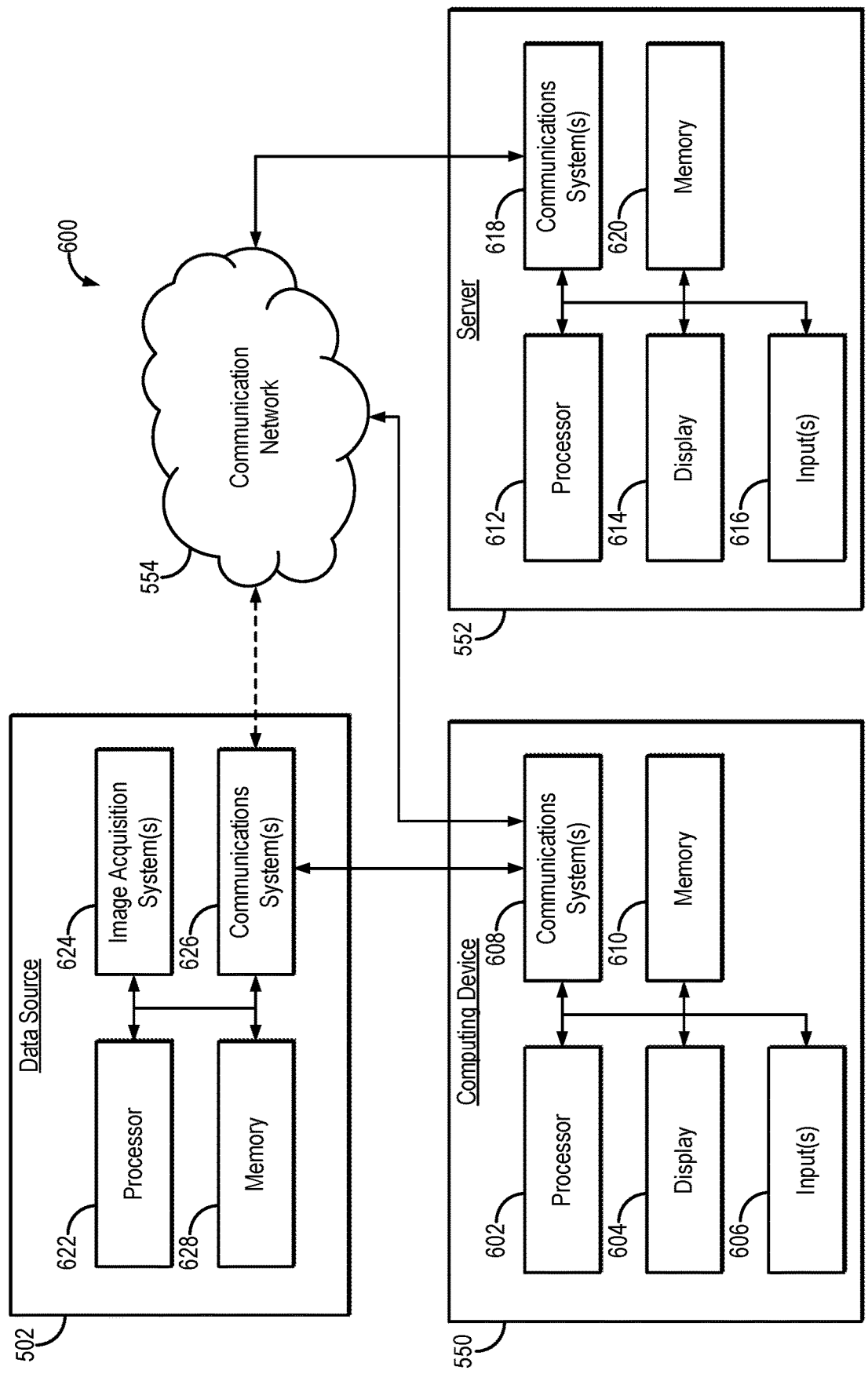
FIG. 6 is a block diagram of components that can implement the system of FIG. 5.

Referring now to FIG. 6, an example of hardware 600 that can be used to implement data source 502, computing device 550, and server 552 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, data source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include an MRI system. Additionally or alternatively, in some embodiments, one or more image acquisition systems 624 can include any suitable hardware, firmware, and/or software for coupling to and/or controlling operations of an MRI system. In some embodiments, one or more portions of the one or more image acquisition systems 624 can be removable and/or replaceable.

Note that, although not shown, data source 502 can include any suitable inputs and/or outputs. For example, data source 502 can include input devices and/or sensors that can be used to receive user input, such as a keyboard, a mouse, a touchscreen, a microphone, a trackpad, a trackball, and so on. As another example, data source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/ or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of data source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 7:
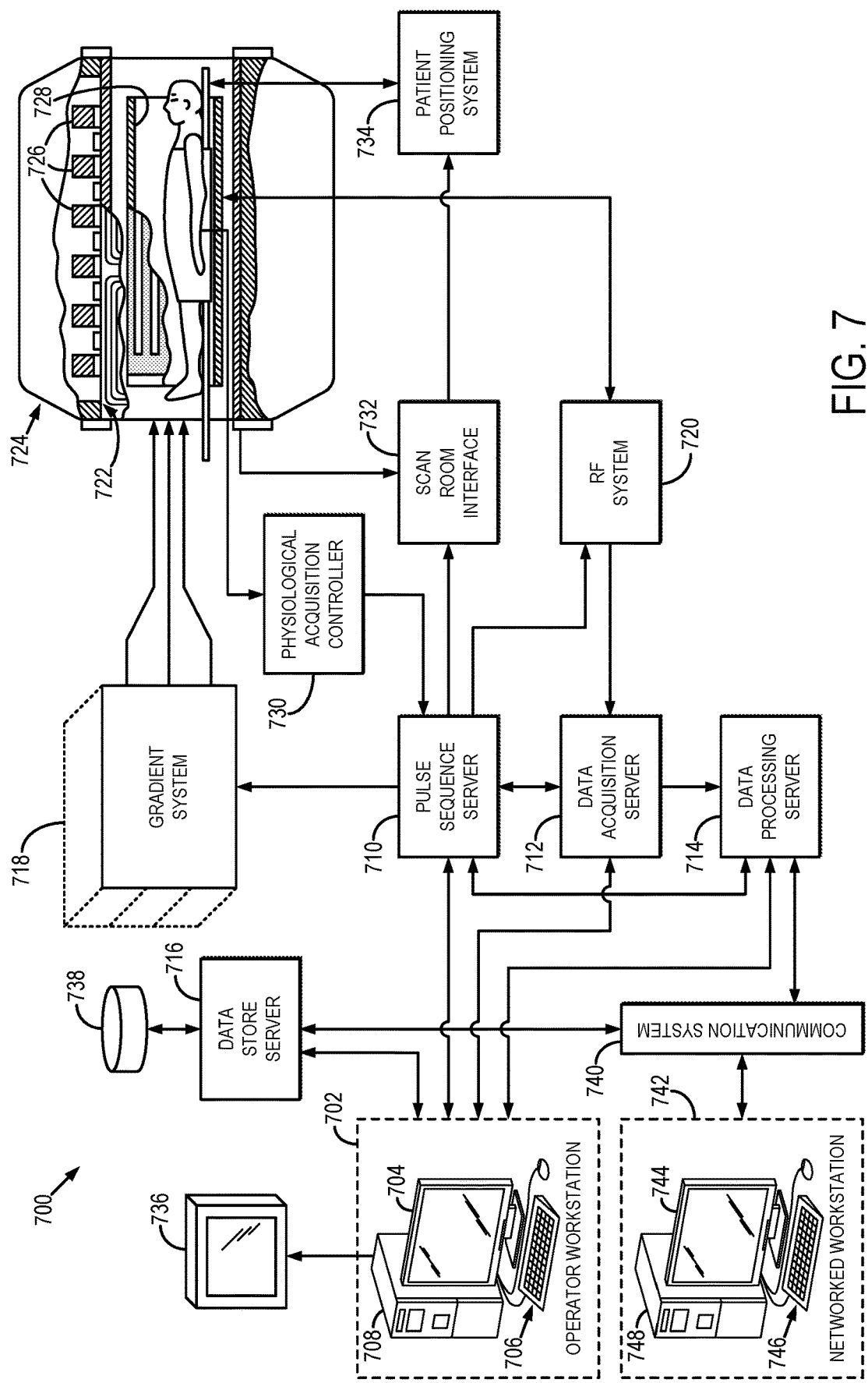
FIG. 7 is a block diagram of an example MRI system that can implement methods described in the present disclosure.

Referring particularly now to FIG. 7, an example of an MRI system 700 that can implement the methods described here is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The pulse sequence server 710 functions in response to instructions provided by the operator workstation 702 to operate a gradient system 718 and a radiofrequency ("RE") system 720. Gradient waveforms for performing a prescribed scan are produced and applied to the gradient system 718, which then excites gradient coils in an assembly 722 to produce the magnetic field gradients $G_x$, $G_y$, and $G_z$ that are used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} ; \quad (6)$$

and the phase of the received magnetic resonance signal may also be determined according to the following relationship:

$$\varphi = \tan^{-1}\left(\frac{Q}{I}\right). \quad (7)$$

The pulse sequence server 710 may receive patient data from a physiological acquisition controller 730. Byway of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heart beat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data is not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

The present disclosure has described one or more preferred embodiments, and it should be appreciated that many equivalents, alternatives, variations, and modifications, aside from those expressly stated, are possible and within the scope of the invention.

The invention claimed is:

1. A method for reconstructing an image with reduced motion artifacts from k-space data acquired with a magnetic resonance imaging (MRI) system, the method comprising:
    (a) accessing k-space data with a computer system, the k-space data having been acquired from a subject using a magnetic resonance imaging (MRI) system, wherein the k-space data contain motion errors associated with motion of the subject;
    (b) reconstructing a motion-corrupted image of the subject from the k-space data using the computer system;
    (c) reconstructing a motion-corrected image of the subject from the k-space data using the computer system by:
        inputting the motion-corrupted image to a trained neural network, generating output as a motion artifact image that depicts motion artifacts associated with the motion of the subject;
        generating a difference image by subtracting the motion artifact image from the motion-corrupted image;
        computing motion parameters that define one or more motion trajectories from the difference image and the k-space data; and reconstructing the motion-corrected image of the subject by inputting the k-space data and the motion parameters to a model-based image reconstruction algorithm, generating output as the motion-corrected image.

2. The method of claim 1, wherein the motion parameters are computed by minimizing a data consistency error between the acquired k-space data and estimated k-space data generated by applying a motion-inclusive forward model to the difference image.

3. The method of claim 2, wherein the motion parameters are computed by minimizing a single cost function.

4. The method of claim 2, wherein the motion parameters are computed using a separable cost function that is separated into a plurality of smaller subproblems.

5. The method of claim 4, wherein the k-space data comprise multi-shot k-space data acquired using a multi-shot pulse sequence and wherein each of the plurality of smaller subproblems optimize motion parameters for a different shot of the multi-shot acquisition.

6. The method of claim 5, wherein each subproblem minimizes a difference between k-space data acquired for a given shot of the multi-shot acquisition and estimated k-space data generated by applying a motion-inclusive forward model specific to the given shot to the difference image.

7. The method of claim 5, wherein the separable cost function accounts for intra-shot motion by assigning additional motion parameters to individual lines of k-space data within each shot of the multi-shot acquisition.

8. The method of claim 7, wherein each subproblem minimizes a difference between k-space data acquired for a given line of k-space in a given shot of the multi-shot acquisition and estimated k-space data generated by applying a motion-inclusive forward model specific to the given line of k-space in the given shot to the difference image.

9. The method of claim 1, wherein the trained neural network comprises a convolutional neural network.

10. The method of claim 1, wherein the trained neural network is trained on training data to detect motion artifacts in a magnetic resonance image, wherein the training data comprise simulated motion-corrupted images and associated simulation motion parameters.

11. The method of claim 1, wherein the trained neural network comprises an input layer, one or more hidden layers, and an output layer, wherein the input layer contains a first input channel for receiving a real part of the motion-corrupted image and a second input channel for receiving an imaginary part of the motion-corrupted image, and wherein the output layer contains a first output channel for outputting a real part of the motion artifact image and a second output for outputting an imaginary part of the motion artifact image.

12. The method of claim 1, wherein the motion-corrected image is iteratively reconstructed by iteratively repeating step (c) such that the motion-corrected image output from the model-based image reconstruction algorithm is stored as an updated motion-corrupted image at each iteration until a stopping criterion is satisfied.

13. The method of claim 12, wherein the stopping criterion is a maximum number of iterations.

14. The method of claim 12, wherein the stopping criterion is a threshold change between the motion-corrected image output from the model-based image reconstruction and the updated motion-corrupted image.

15. The method of claim 1, further comprising displaying the motion-corrected image to a user using the computer system.

16. The method of claim 1, wherein the computed motion parameters are rigid-body motion parameters.

17. The method of claim 1, wherein the computed motion-parameters are non-rigid-body motion parameters.

* * * * *